(12) United States Patent
Wu

(10) Patent No.: US 7,943,901 B2
(45) Date of Patent: May 17, 2011

(54) PRACTICAL ION MOBILITY SPECTROMETER APPARATUS AND METHODS FOR CHEMICAL AND/OR BIOLOGICAL DETECTION

(75) Inventor: Ching Wu, Acton, MA (US)

(73) Assignee: Excellims Corporation, Acton, MA (US)

( * ) Notice: Subject to any disclaimer, the term of this patent is extended or adjusted under 35 U.S.C. 154(b) by 530 days.

(21) Appl. No.: 11/946,679

(22) Filed: Nov. 28, 2007

(65) Prior Publication Data

US 2008/0121797 A1    May 29, 2008

Related U.S. Application Data

(60) Provisional application No. 60/867,400, filed on Nov. 28, 2006.

(51) Int. Cl.
*H01J 49/04* (2006.01)
*H01J 49/40* (2006.01)
*H01J 49/10* (2006.01)

(52) U.S. Cl. ........ 250/288; 250/281; 250/282; 250/286; 73/864.91

(58) Field of Classification Search .................. 250/288, 250/281, 282, 286; 73/864.91
See application file for complete search history.

(56) References Cited

U.S. PATENT DOCUMENTS

| | | | |
|---|---|---|---|
| 7,057,168 B2 * | 6/2006 | Miller et al. .................. 250/287 |
| 7,132,650 B1 * | 11/2006 | Gamble et al. ................ 250/288 |
| 7,576,321 B2 * | 8/2009 | Wu ............................... 250/286 |
| 2004/0021071 A1 * | 2/2004 | Mordekhay .................... 250/288 |
| 2005/0189486 A1 | 9/2005 | Fuhrer |
| 2005/0205775 A1 | 9/2005 | Bromberg |
| 2006/0151687 A1 | 7/2006 | Miller |
| 2009/0278040 A1 * | 11/2009 | Wu ............................... 250/282 |

* cited by examiner

*Primary Examiner* — Nikita Wells

(57) ABSTRACT

This invention describes an ion mobility spectrometer system for chemical detection in the field. The system allows: a high throughput operation, an interface to new ionization methods, and an interface to a mass spectrometer.

21 Claims, 14 Drawing Sheets

View A    View B

PRACTICAL ION MOBILITY SPECTROMETER APPARATUS AND METHODS FOR CHEMICAL AND/OR BIOLOGICAL DETECTION

CROSS-REFERENCE TO RELATED APPLICATIONS

The present application claims the benefit of and priority to corresponding U.S. Provisional Patent Application 60/867,400 filed Nov. 28, 2006, the entire content of the application is herein incorporated by reference.

BACKGROUND OF THE INVENTION

Many chemical and/or biological analytical instruments that are currently used for sample analysis have many limitations. Some areas that are currently deficient are: the ability to quickly analyze a sample using a compact instrument in a high throughput manner, an efficient and effective sampling method, and an effective manner to interface multiple analytical instruments. A comprehensive instrumental approach can address chemical and/or biological detection issues in many areas/applications such as pharmaceutical, environmental, and food industry, as well as homeland security, in particular home made explosives, liquid detection needs with adaptability to future threats. A comprehensive instrumental approach on ion mobility spectrometer (IMS) apparatus and methods offer all of the following advantages: improved throughput compared to current detection systems; adaptability to new ionization methods that can be used to introduce samples in different categories of chemicals in vapor, liquid and particle forms; enhanced capability for detecting labile chemicals, such as homemade explosives TATP, nitroglycerine and PETN; and an interface to mass spectrometers (MS) that will enhance field performance of future MS based field detection systems.

Ion mobility based spectrometers need to utilize various methods and components to be able to analyze samples in a high throughput manner and/or operate in a portable design. Current ion mobility based spectrometers require complicated mechanically designed parts for construction of the drift tube, whereby each component in the drift tube requires multiple parts and produces an overall high power consumption system. The high power consumption significantly limits the performance of the ion mobility based spectrometer. One aspect of the present invention relates to ion mobility based spectrometer systems for continuous sampling operations, rapid temperature control/temperature gradient analysis, and low power consumption portability.

In practical chemical detection, such as explosive detection, applications, the two major challenges to a given analytical instrument are system effectiveness and readiness. Even though existing IMS based trace detection systems can meet the current throughput requirements at airport checkpoint, these detection systems need to have much higher throughput in order to handle the detection requirements for mass transit applications.

Ion mobility based spectrometers (IMS) and MS utilize various methods to introduce the vapor of a sample into the analysis chamber and/or ionization chamber of the given instrument. For example liquid samples can be injected via a syringe and thermally vaporized. Whereas solid samples are commonly vaporized via thermal desorption. Many different methods can be utilized, the chemical nature of the sample generally influences the method used. Heating samples to elevated temperatures in order to vaporize them can be destructive. Since the currently used methods for heating the samples in an IMS range between 220° C. and 300° C., decomposition can occur at these elevated temperatures. For example, the explosive 1,1-diamino-2,2-dinitroethylene (FOX-7) decomposes at 238° C.

SUMMARY OF THE INVENTION

The present invention generally relates to systems and methods of analyzing samples using a chemical and/or biological analytical instrument, in particular this invention addresses current issues of chemcial detection/analysis by developing a comprehensive detection system based on an integrated IMS that could be used for explosive detection for scenarios under high throughput conditions. Interfacing the IMS to new ionization methods that can be used to introduce different categories of explosives and using the IMS to bridge the sampling system and concept of operations for IMS to MS based detection systems, thus enhancing and enabling the fieldablity of MS based detectors. The subject matter of the present invention involves, in some cases, interrelated products, alternative solutions to a particular problem, and/or a plurality of different uses of one or more systems and/or articles.

In one aspect of the invention, a high throughput trace detector (HTTD, this term sometime is used interchangeable with IMS) is based on high thermal conductivity ion mobility spectrometers (HTCIMS). The unique configuration of the HTCIMS allows rapid change of detector temperature thus enabling time-temperature desorption methods and TRUE temperature ramping in the trace detection process. True temperature ramping enables higher sensitivity and selectivity for thermally labile explosives. The low thermal mass construction of the HTCIMS will also allow rapid system clean up in seconds, which eliminates system down time in high throughput detection applications. In addition, the low thermal mass construction allows a lower overall power consumption system that is useful for portable detection applications. In another set of embodiments, the invention uses the HTCIMS to eliminate detector memory effects and achieve simultaneous temperature ramping of desorber and IMS detector; this innovative detection system will improve capabilities of IMS based trace detection systems and provide a device that has higher throughput and greater detection effectiveness for explosive detection.

In yet another set of embodiments, the IMS system is equipped with chemically assisted thermal desorption (CATD) capability to control the fragmentation pathway during the temperature programmed desorption. CATD desorbs explosives under controlled chemical environments. During the desorption process, unstable explosives undergo known decomposition paths, resulting in predictable and detectable fragment ions in the HTCIMS. CATD can greatly enhance system sensitivity and specificity of peroxide detection, especially for HMTD that is known for rapid decomposition during the thermal desorption process.

In another aspect of the invention, the capability of the HTTD will be further improved by allowing modernized ionization methods to be utilized. With electrospray ionization, black powers and other inorganic explosives can be reliably detected. The invention describes a combined thermal desorber and electrospray unit without additional mechanical components and pumps. The new HTTD has a multi-function sample introduction apparatus that can also accommodate multiple sample introduction ports for introducing samples in vapor, liquid and solid phases. The liquid injection port can be used to analyze unknown liquids with minimal sample preparation. In addition, the compatibility of other new ionization methods, such as DESI and DART may be used.

In another set of embodiments, the HTTD will be developed as an interface to MS. With versatile sample introduction and high throughput performance, the HTTD as a front end will eliminate many problems when converting laboratory MS systems to field chemical detection applications. One of the major issues for tandem IMS-MS is the ion transportation efficiency between high pressure IMS and high vacuum MS. HTTD-MS will address this issue with three electric field zone extraction. The integrated HTTD-MS system not only has the potential for being used as an advance trace detection system, but also can be become the benchmark used to evaluate the performance of all other ETDs used in explosive detection applications.

In yet another set of embodiments, a multi-function sample introduction apparatus can be used for: thermal desorption of solid samples on a substrate or from a removable sample holder, electrospraying liquid samples from a liquid inlet, and electrospraying a sample from a removable sample holder.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

DETAILED DESCRIPTION OF VARIOUS EMBODIMENTS

Figure 1:
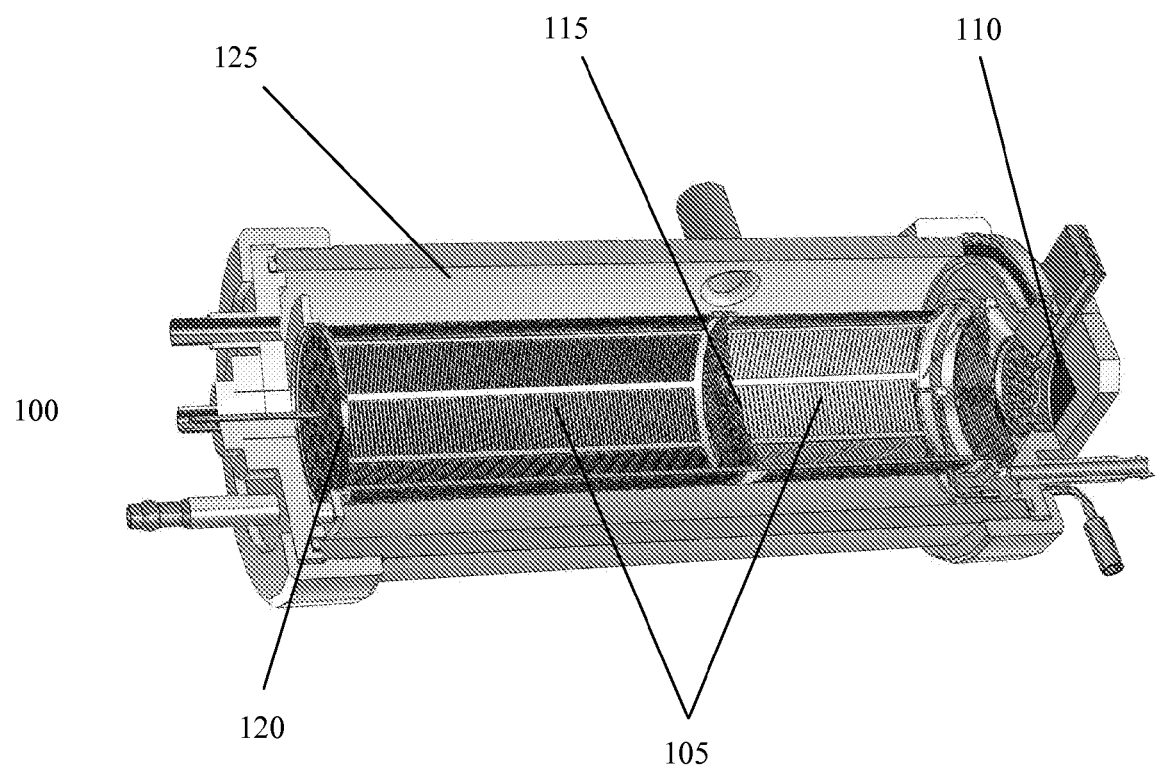
FIG. 1 schematically shows one example of a low thermal mass IMS using a resistance coil structure.

As used herein, the term "analytical instrument" generally refers to ion mobility based spectrometer, MS, and any other instruments that have the same or similar functions.

Unless otherwise specified in this document the term "ion mobility based spectrometer" is intended to mean any device that separates ions based on their ion mobilities or mobility differences under the same or different physical and chemical conditions and detecting ions after the separation process. Many embodiments herein use the time of flight type IMS, although many features of other kinds of IMS, such as differential mobility spectrometer and field asymmetric ion mobility spectrometer are included. Unless otherwise specified, the term ion mobility spectrometer or IMS is used interchangeable with the term ion mobility based spectrometer defined above.

Unless otherwise specified in this document the term "mass spectrometer" or MS is intended to mean any device or instrument that measures the mass to charge ratio of a chemical/biological compounds that have been converted to an ion or stores ions with the intention to determine the mass to charge ratio at a later time. Examples of MS include, but are not limited to: an ion trap mass spectrometer (ITMS), a time of flight mass spectrometer (TOFMS), and MS with one or more quadrupole mass filters.

The phrase "and/or," as used herein in the specification and in the claims, should be understood to mean "either or both" of the elements so conjoined, i.e., elements that are conjunctively present in some cases and disjunctively present in other cases.

The present invention generally relates to systems and methods of analyzing samples using a chemical and/or biological analytical instrument, in particular this invention addresses current issues of explosive detection by developing a comprehensive detection system based on common core technologies: a high thermal conductivity material and/or a low thermal mass construction, a novel sample introduction system, and a novel instrument interface system. All of these novel features ether together or used separately improves the currently used technology. The subject matter of the present invention involves, in some cases, interrelated products, alternative solutions to a particular problem, and/or a plurality of different uses of one or more systems and/or articles.

In one set of embodiments of the invention, a HTTD is based on high thermal conductivity ion mobility spectrometers (HTCIMS). The unique configuration of the HTCIMS allows rapid change of detector temperature thus enabling time-temperature desorption methods and TRUE temperature ramping in the trace detection process. True temperature ramping enables higher sensitivity and selectivity for peroxides detection, as well as other thermally labile explosives. The low thermal mass construction of the HTCIMS will also allow rapid system clean up in seconds, which eliminates system down time in high throughput trace detection applications. In addition, the low thermal mass construction allows a lower overall power consumption system that is useful for portable detection applications.

In another set of embodiments, the configuration of the HTCIMS, a variety of ionization methods, including but not limited to radioactive ionization, corona discharge, electrospray, desorption electrospray, DART, secondary electrospray ionization, photo ionization and etc., will be used to ionize targeted chemicals. The ionization source structure will also be designed to accommodate multiple ionization methods.

In some embodiments, the low thermal mass constructed analytical instrument 100 is shown in FIG. 1. The drift tube and reaction region is made from a wrapped resistance coil 105 that allows rapid temperature gradients, either heating and/or cooling. The other components shown in FIG. 1 include; a thermal desorber 110, an ion gate 115, a Faraday ion collector 120, and a protective tube 125.

The resistance coil ion mobility based spectrometer (RCIMS) uses helical resistive material to form constant electric fields that are used to guide ion movements in an IMS. This drift tube for IMS is constructed with a non-conductive frame, continuous resistance wires, an ion gate assembly, a protective tube, flow handling components, an ion detector assembly, and other components. The resistance wires are wrapped on the non-conductive frame form coils in a round (or polygon) shape. The coil generates an even and continuous electric field that guides ion drift through the IMS. The resistance wires are not only used to form the electric field, they also function as the heating element to heat up the drift tube. The IMS design controls drift tube temperature using the resistive coil to maintain drift gas temperature; a separate heating element is used to preheat the drift gas before entering the drift region. The drift gas is delivered directly inside the coil and pumped away from the gas exit on the protective housing. This configuration provides a robust IMS that is simple to build with extremely low thermal mass along the ion and drift gas path, thus allowing rapid temperature changes. In summary, the drift tube design enables the IMS to be build with lower weight, lower power consumption, lower manufacturing cost, and is completely free of sealants that may out gas causing manufacturing problems for conventional spectrometers. An example configuration of a RCIMS: using 51 gauge Alloy COJ to construct a drift tube of 1.5 inch in diameter and 4 inch long, the total resistance is 1.4 Mohm; power consumption of 4.7 W at a drift field strength of 250 V/cm.

The RCIMS can be operated in either positive or negative ion mode, or a rapid switching mode (note that the basic concept of polarity switching has no patent infringement issue). With much lower total resistance, the drift field can be established much faster compared to common drift ring designs. The linked desorber-detector temperature ramping is achieved by continuously increasing voltages on the coil over ionization and reaction regions. In addition, if the drift voltage is also ramped in the same fashion, additional information could be generated by analyzing kinetics of ion decomposition reactions and transportation properties to gain higher specificity for explosives detection. At the end of each temperature ramping program, the spectrometer can be completely cleaned up by increasing the voltage across the spectrometer: a) all residue ions in the drift tube will be accelerated and neutralized on the collector; b) the coil temperature may increase to 500-600° C., thus all chemical residues on the wall of the drift tube will be evaporated into purge flow or decomposed (note the Alloy COJ has a melting point of 1200° C.).

In addition, with electrical current passing through the resistance wires, the coil can create a magnetic field inside the spectrometer. This magnetic field is used to effect ion movements in the RCIMS. With the effects of ion focusing and de-focusing, two-dimensional separation can be achieved by adjusting the electric and magnetic field conditions inside the drift tube. In the RCIMS design, the ions can be pushed out of the ionization source through a much smaller opening. After entering the drift region, the ions will not only drift down the drift tube under influence of the electric field, but also move in a circular motion because of the circular component of the electric field generated by the resistance coil. When the ions cut through the magnetic field, they are pushed toward the coil. The strength of the force is related to the speed of the ions which is determined by their ion mobilities. Therefore, ions with different mobility are detected at different locations on the Faraday plate. A Faraday plate that consists of multiple concentric rings can be used for obtaining the two-dimensional separation data. The 2D detection approach can improve the detector specificity and reduce false alarm rates.

Figure 2:
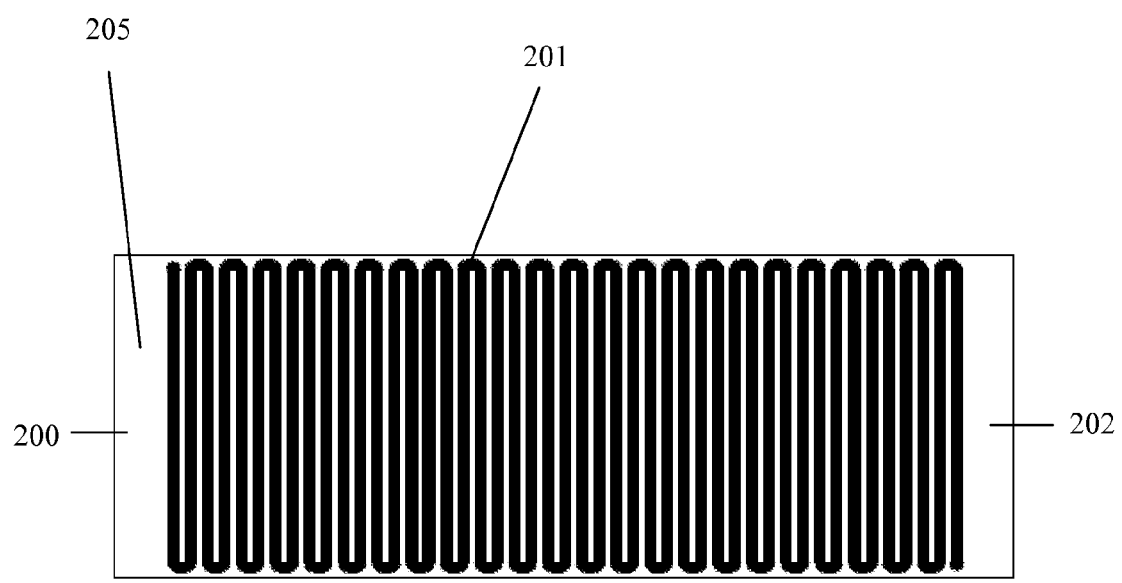
FIG. 2 schematically shows an example of low thermal mass component for IMS using a resistive material affixed on a dielectric substrate.

In one set of embodiments, the low thermal mass structure is a resistive material 201 affixed on a non-conductive (dielectric) wall 205 as shown in FIG. 2. The term affixed should be understood to mean deposited on the surface though process, such screen printing or thin film deposition. The wall could be made of non-conductive material including, but not limited to, ceramic, fused silica, quartz. In particularly, highly thermal conductive and dielectric material including, but limited to, beryllium oxide (BeO) and aluminium nitride (AlN) represents the best choice. However, other materials, such as alumina ($Al_2O_3$) or any other kind of ceramics has suitable electrical properties and mechanical structures can also be used for the analytical instrument construction. In a variety of embodiments, the resistive material can be arranged in, but not limited to, a serpentine line (as illustrated in FIG. 2), multiple lines that are substantially parallel straight or curved from the first end 200 to the second end 202 of the wall. The analytical instrument can be assembled using one or multiple pieces of wall structure. The wall could be in any shape that is suitable for constructing the analytical instrument including, but limited to, a flat plate, a curved plate, a round tube, a half round tube, a rectangular tube.

Figure 3:
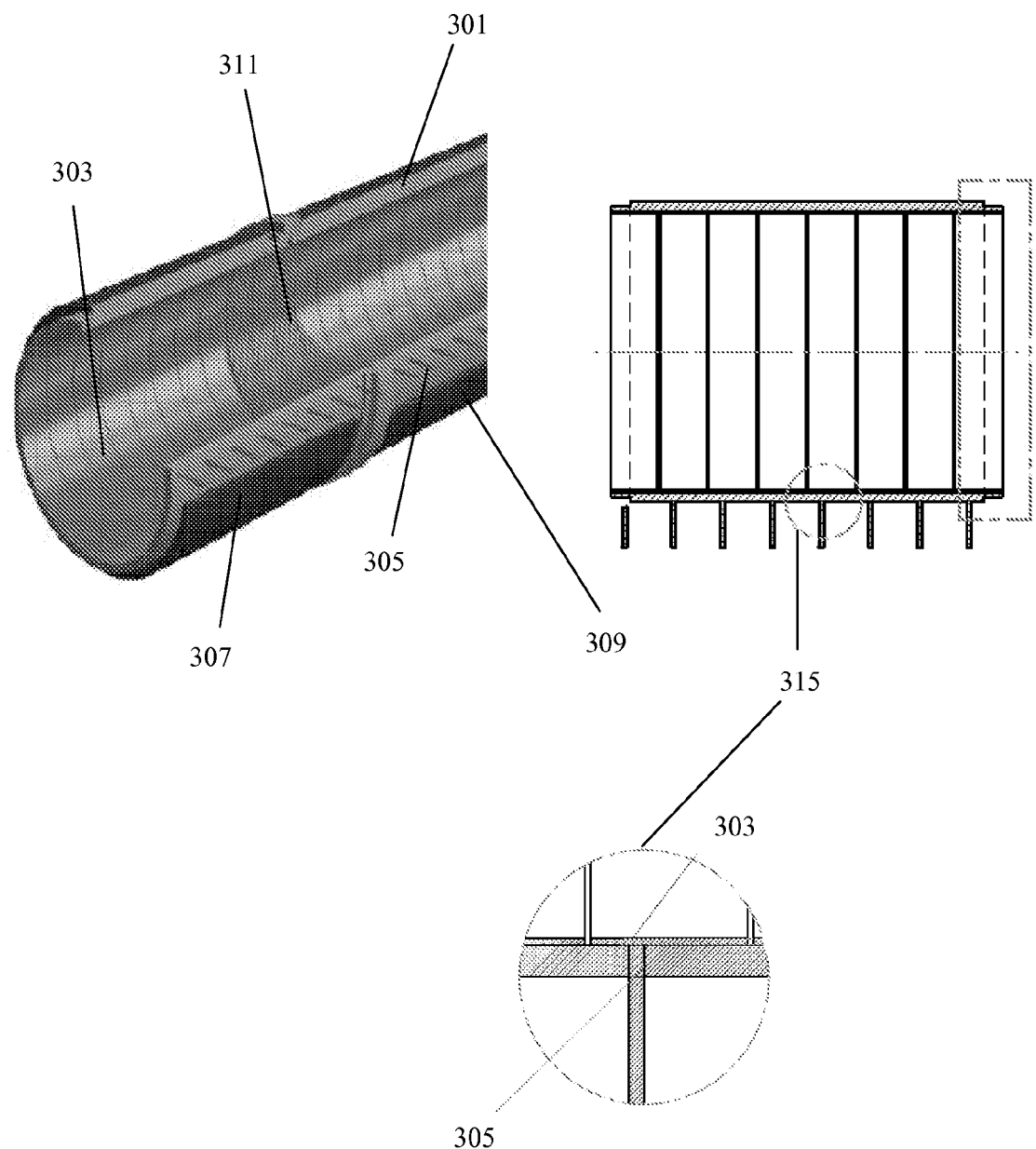
FIG. 3 schematically shows a IMS using a metalized dielectric structure and details of the leading electrical contacts in the IMS construction.

Yet another aspect of the present invention is the IMS using a metalized dielectric structure to create necessary electrode layout for generating electric field in the IMS. A metalized dielectric tube is shown in FIG. 3. To realize the design as shown in this figure, the dielectric tube 301 is first machined for between inner and outer surface quality; array of holes for the leading electrical contacts are also prepared 315; and then, the entire inner surface is coated with single or multiple layer to metallization materials. The metallization process is commonly finished with a thin layer of nickel, gold or other inert metal for enhanced chemical resistivity. The metalized inner wall of the tube is then machined into rings by removing a narrow gap of the metal layer (as shown in FIG. 3). The metalized rings on the inner wall 303 of the tube are connected to the power supply via array of electrical contact wires 305 through the holes on the wall. An ion gate 311 is also shown in FIG. 3. A heater 307 and a heat sink component 309 for cooling are tightly mounted on the outer wall of the dielectric tube. As high thermal conductivity ceramic will be used for this contraction, the heating and cooling process is expected to be accomplished within seconds. Without pursuing the highest heating and cooling rate, the ceramic material can be 92 to 99.9% alumina, $Al_2O_3$, or any other kind of ceramic that has suitable electrical and mechanical properties. For optimized thermal conductivity, aluminum nitride (AlN) can be used as the base ceramic tube for the drift tube structure. Beyond the examples given above, other dielectrics with high thermal conductivity and the proper dielectric constants could also be used for the IMS drift tube construction.

Figure 4:
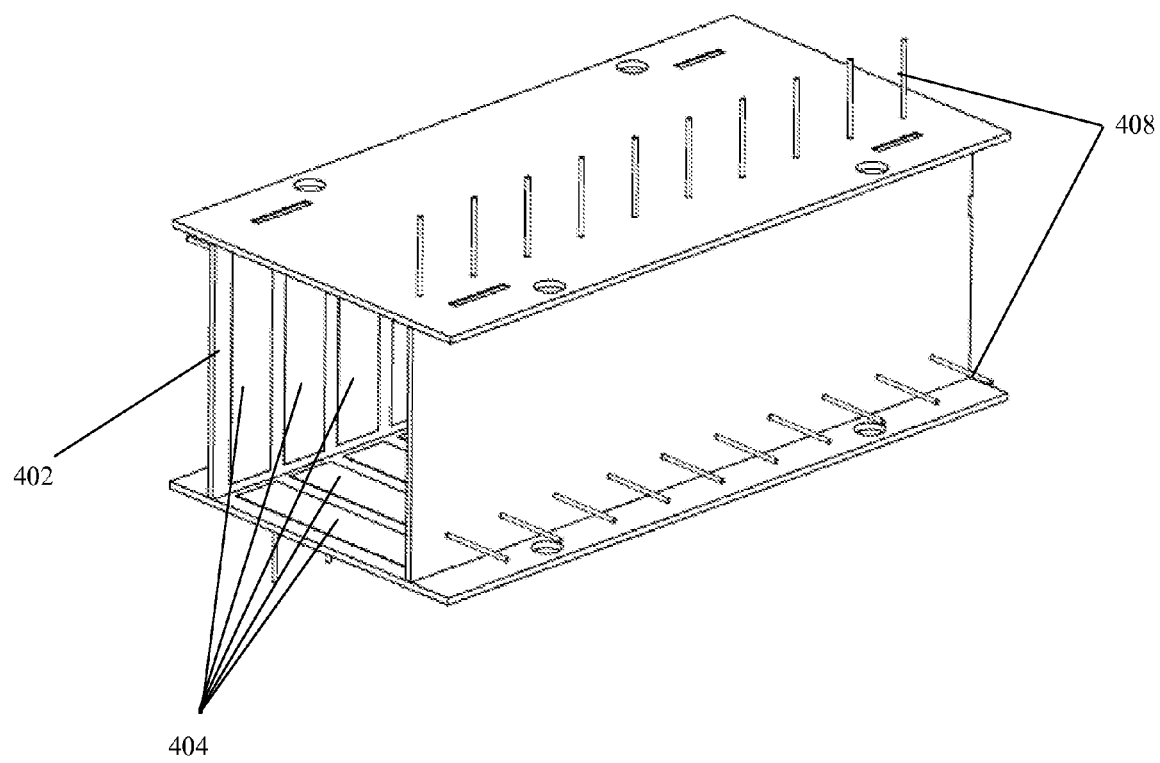
FIG. 4 schematically shows a IMS using a metalized dielectric structure that consists of multiple dielectric substrate components; in particular the metalized dielectric substrates are substantially flat.

In one set of embodiments, the IMS using a metalized surface on a substantially flat dielectric material, such as ceramic, but not limited to this material is shown in FIG. 4. In addition, the dielectric material (substrate) does not necessarily need to be flat, but can include a curved shape. A thin layer of nickel, gold or other inert metal 404 for enhanced chemical resistivity is formed directly on the substrate 402 using an additive method such as screen printing and thin film deposition to each inner wall. Conductive leading contacts 408 are either extensions of metalized pads or bonded lead wires. The flat plates can be assembled into an enclosed chamber for use in an IMS spectrometer. The assembled shape of the metalized flat plates shown in FIG. 4 is rectangular, although the metalized flat plates can be assembled into any useful shape, in particular, square. The assembled 4 plates can have metalized pads that are: individual, partially connected forming a partial ring structure, and interconnected to each other forming a full ring structure. In the case of the interconnected or partially connected metalized pads, the number of lead contacts or wires used may be less then when employing individual metalized pads. A heating element or heating elements can be arranged surrounding the enclosed chamber or mounted on one or more plate(s) in case high thermal conductivity materials used for the construction of the entire plate can serve as a heater for the enclosed chamber. Reduced thermal mass of this device can be achieved by choosing high thermal conductivity substrate and reducing physical dimension of components and overall device.

Figure 5:
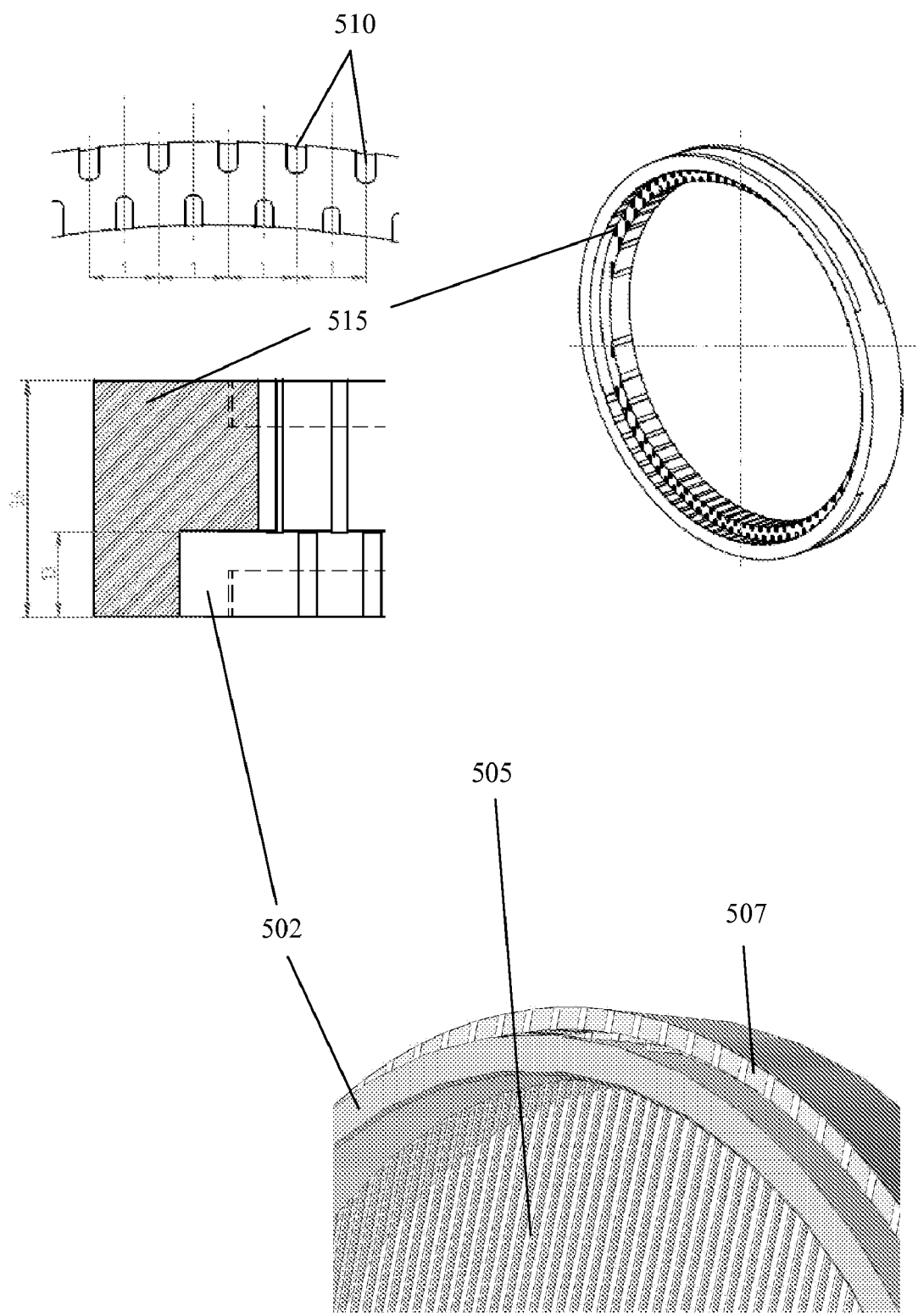
FIG. 5 schematically shows a construction of a Bradbury-Nielsen ion gate using metalized dielectric rings and parallel wires.

In one embodiment, components of an IMS using a metalized ceramic material is shown in FIG. 5. FIG. 5 shows a unique construction method of a Bradbury-Nielsen ion gate. It is built with a frame ring, a tension ring 502 and parallel wires 505 that are pre-winded on a metal frame. One or the rings, either the frame ring or the tension ring is metalized 515 with a pattern 510 that connects every other wire to each other. In one embodiment, the frame ring has metalized contacts 507 that are 1 mm apart (center to center). During the ion gate construction, the parallel wires are lined up with these contacts and form a firm contact while the tension ring is pushed down into the frame ring. As the wire is selected to match the thermal expansion of the frame ring and tension ring, the wires can be maintained parallel while the IMS is operated under different temperature conditions. The gate control voltage(s) are applied to the wires by attaching an electrical lead to the contact point that is on the outside of the frame ring. Not only for metalized ceramic tube IMS design, the Bradbury-Nielsen ion gate can be used for other analytical instruments.

Figure 6:
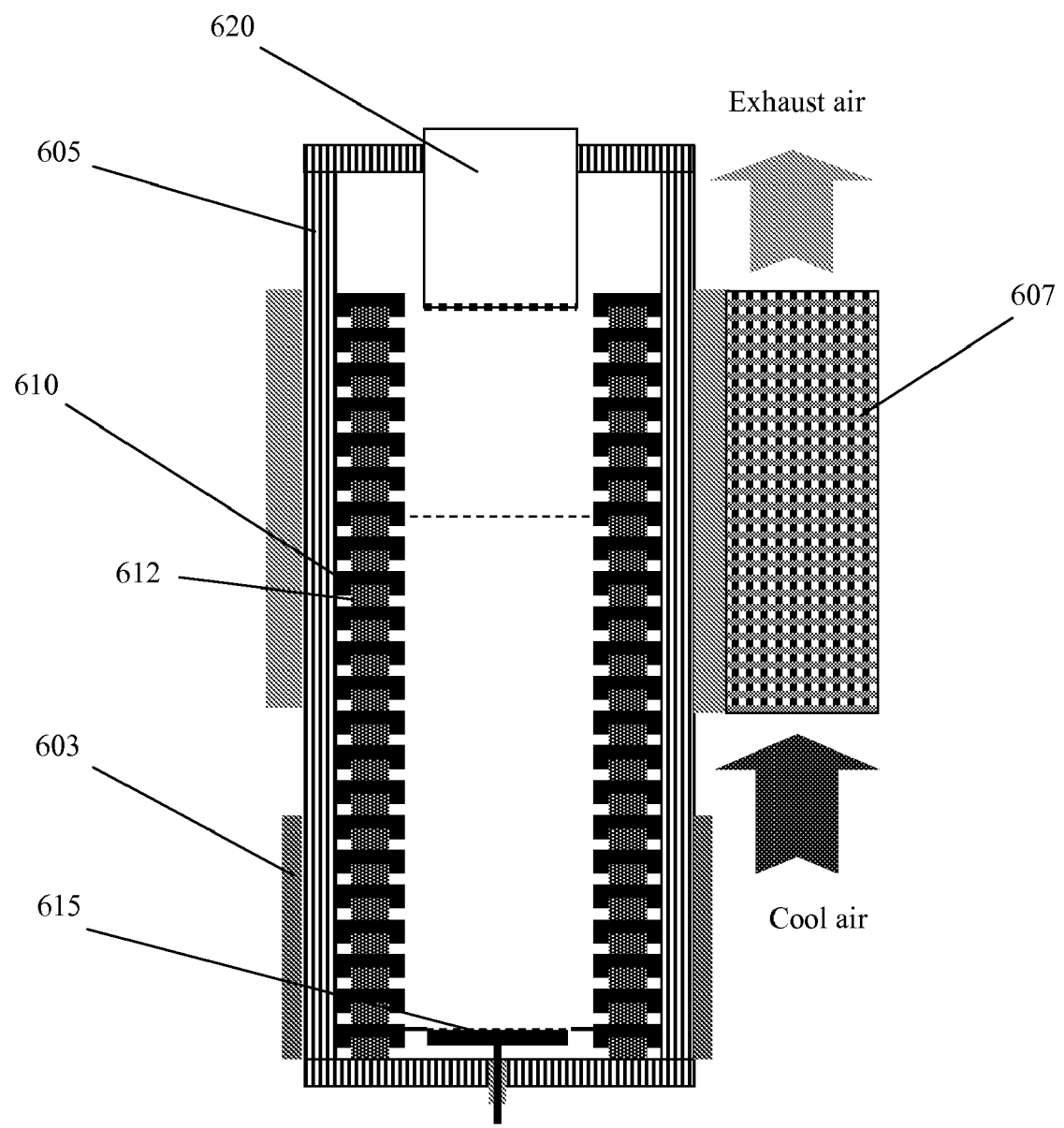
FIG. 6 schematically shows a stack ring design using high thermal conductive electrodes (metal) and dielectric spacers that allow rapid heating and cooling of the apparatus using a heat pump.

In another embodiment, the invention using the HTCIMS has a stack ring design IMS; this device is designed and constructed using high thermal conductive electrodes (metal or metal coated components) and insulation materials (dielectric) for rapid heating and cooling methods. A heat sink with cooling means will be used to rapidly pump away the excessive heat after each heating cycle. FIG. 6 shows one embodiment that uses a heating belt 603 that is mounted on a dielectric structure 605 and a forced air heat pump 607 to rapidly heat and cool the device. A heat pump as used herein is a device to add or remove heat from analytical instrument. Unrelated to the specific example shown in this figure, the heat pump can be used on any IMS device and/or analytical instrument. The heat can also be added or removed from a device via a media, such as gas or liquid. An ion detector 615 and an ionization source 620 are pictured, although both of these elements of the instrument could be used externally. A drift gas preheating element (not shown in the figure) is also used to work cooperatively with the drift tube temperature control components described above. Instead of traditional stainless steel guard rings used in many previous art IMS, the HTCIMS uses high thermal conductivity metals and/or alloys for the guard ring construction 610, i.e. gold coated aluminum rings, but not limited to these. The spacer between guard rings 612 are also made of high thermal conductivity materials, i.e. AlN, but not limited to this. With the HTCIMS, the heating and/or cooling of the device from 50 to 350° C. can be achieved within several seconds. In trace detection applications, the rapid heating and cooling is used to perform synchronized thermal desorber-IMS temperature ramping, on-the-fly desorber and IMS clean up, declustering ions in unwanted form during IMS measurements and study ion chemistry in the drift tube. One method for operating the low thermal mass IMS comprises: rapidly adjusting an IMS temperature to the first starting operating temperature and then ramping the temperature to the ending operating temperature at a designed rate using the heat pump. This method of ramping the temperature can be done while, before, or after obtaining ion mobility spectra. This method can also include: ramping temperature of a thermal desorber that is in fluid communication with a sample inlet of the IMS wherein the design rate of the IMS temperature ramping is substantially equal to or higher than the desorber temperature ramping rate. This method of temperature ramping can also be used for cleaning the IMS in-between sample runs.

Figure 7:
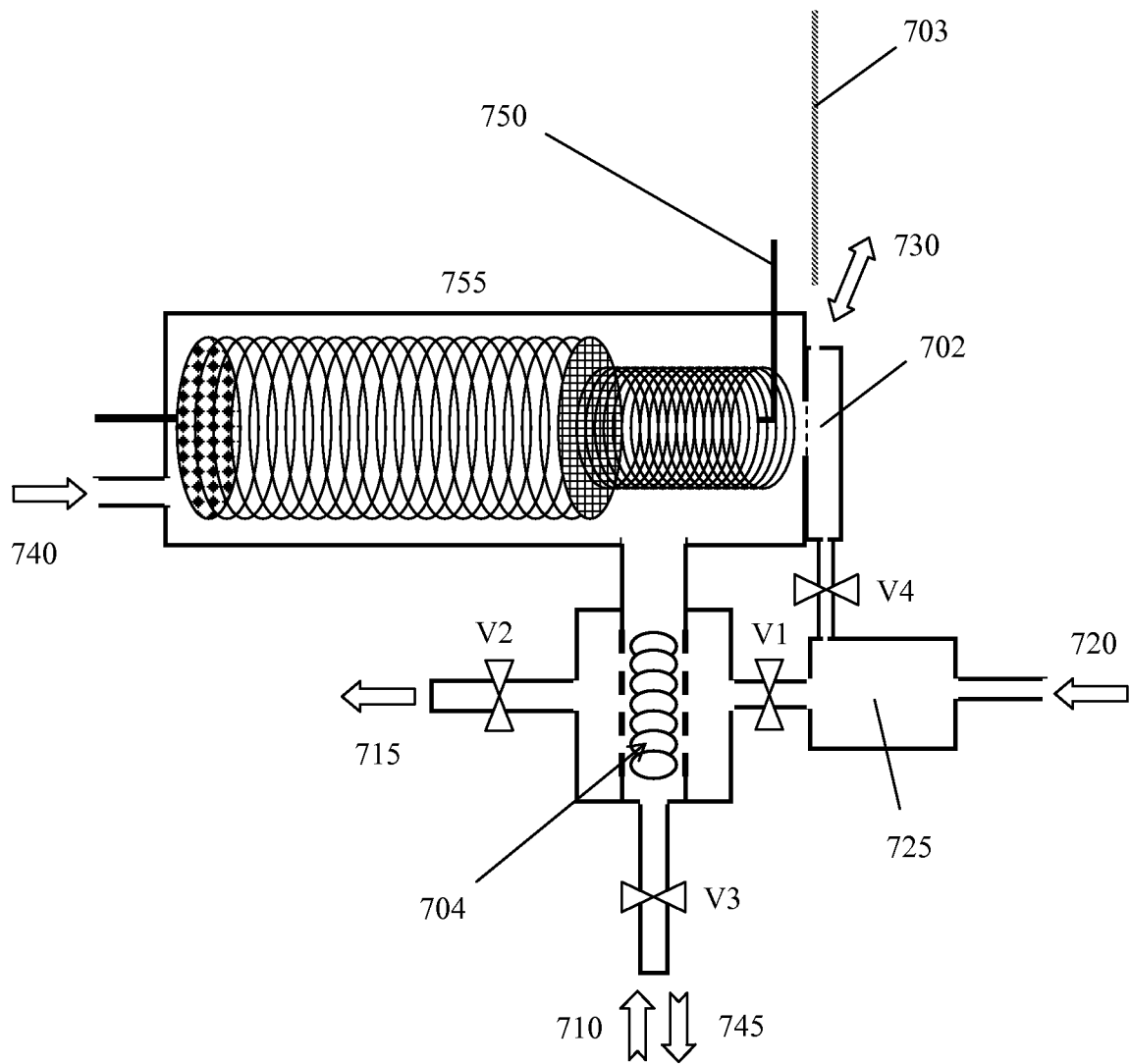
FIG. 7 schematically shows a chemical assistant thermal desorption apparatus that chemically modifies the environment during thermal desorption of samples on a swab and/or a preconcentrator.

In another set of embodiments of the invention, FIG. 7 shows the apparatus of the HTCIMS with a thermal desorber 702 for swiped (swabbed using dry or wet swabs) sample 703 and a preconcentrator 704 for vapors and particles collected from air; this preconcentrator is particular useful for peroxide detection from the gas phase. The home made explosive (HME) vapor preconcentrator is made from plural layer of coils. The coil is made of resistance alloy. The pitch size of the coil is made to precisely trap/filter out certain size of the particles during preconcentration. Multiple coils could be made with different pitch sizes to achieve multiple step filtrations. As shown in FIG. 7, When the sample flow "710" enters the preconcentrator chamber, it pass through the coils (only single layer of coil is shown) and then pumped away with flow "715". The particles of different sizes are trapped on different layer of coils. The vapor sample can be trapped on any coils when interacted with the coil surface. They could be trapped without any affinitive coating as the preconcentrator is at related low temperature. During the sample preconcentration stage of operation, valve V1 is closed, V2 and V3 are open to allow flow to pass design direction. In addition, the affinity layer coating material generally has higher electrical resistance compared to the coil material itself. Thus it can function as insulating layer when electrical current is passing through the coil for flash heating. Different coils or different section of the coil can be coated with different material to trap chemicals of different classes.

During the desorption process, a local chemical environment is created to assist sample desorption/evaporation process. The function of these chemicals is either to directly react with the trapped samples and convert them into IMS detectable form, or to control their fragmentation path way at elevated temperature. To introduce additional chemical to into the preconcentrator, valve "V2 and V3" are closed, V1 is open, thus Gas flow "720" that pass through a chemical chamber 725 is introduced to the preconcentration chamber during the desorption process. During the desorption process, the coils are flash heated with controlled temperature ramping speed to evaporate the trapped chemicals. If the chemicals are not necessary, the desorption flow can be redirected by closing V1 and open V3. There are many thermal labile explosives that decompose before being evaporated, the CATD can be used to create known fragments and subsequentially detected by RCIMS. Similarly, CATD approach can also be used during the desorption of sample on a swipe (substrate) (in this case V1 & V2 are closed and V3 & V4 is open). The airflow 730 will bring desorbed sample into the resistive coil spectrometer 755, the ionization source 750, and both drift flow 740 and sample flow 730 will be purged via V3 through flow 745. The CATD can potentially be a great advantage when used HTTD for peroxide detection. For example, Hexamethylene Triperoside Diamine (HMTD) does not have sensitive response IMS based systems because of the thermal decomposition, however, if the explosive is desorbed in the modified chemical environment that is doped with acidic vapor, a decomposition product can be predicted. In this specific case, the product is peroxy-bis-methanol [Jounal; Legler; CHBEAM; Chem. Ber.; 18; 1885; 3344] that could be sensitively detected by HTTD in the negative ion mode. CATD can not only being used for peroxides detection, but also improve detection of other thermal labile common explosives or taggants.

In yet another set of embodiments of the invention, the sample introduction system is threefold; to add an electrospray method that is compatible with current sampling techniques, add additional sample introduction ports that can be used to directly introduce liquid samples, and combine with other ionization methods, such as DESI and DART for HTTD. The compatible electrospray ionization add-on for HTTD will address one of the major shortcomings of IMS based trace detectors, i.e. detection of low explosives, such as black powers, and other nonvolatile explosives, such as inorganic sodium chloride and ammonium perchlorate. In addition, with the importance and recent interests in touchless sampling, interfacing the HTTD with DESI and/or DART ionization methods may enable the HTTD to collect samples remotely. More importantly, if the ions created by these ionization methods can be effectively introduced into the HTCIMS, then the HTCIMS can be used to isolate the MS system from contaminants that are desorbed from the sampling surface. As most mass spectrometric system are operated at room temperature, desorbed neutral explosive samples and contaminates can easily accumulated at the inlet area other components that are exposed. System clean up and false alarms are anticipated under field operating conditions, especially since many of these ionization methods require high sample flow rate for the desorption ionization.

In some embodiments, a wet sampling scheme, e.g., electrospray ionization can be used to process the wet samples by directly spraying collected sample into the ionization chamber. One implementation of this method includes having the wet samples put into a removable sample holder, which has an electrospray needle and electrodes where an electrospray voltage can be applied. As the sample is sealed inside the holder, pressure is applied to the holder/soaked sample substrate either directly or indirectly, and the solvents and dissolved sample reach the electrospray needle, and are electrosprayed to form highly charged droplets. The electrospray sample ions can be guided into the ionization chamber for analysis. The combination of wet sampling and direct electrospray ionization for the instrument can provide, for example, detection capabilities for both inorganic and organic explosives and other chemicals of interest.

Unless otherwise specified in this document the term "particle" is intended to mean chemical and/or biological single or plurality of atom, molecule, large or macro molecule, nanoparticle, or other matters that are; solid, liquid, crystal, charged species, vapor, droplets, an aerosol, gas, supercritical fluid and/or other fluidic materials or any other medium in which specific molecules of interest may be deposited/applied to a sampling substrate.

Sampling particles from a desired target utilizing a sampling substrate or swab can be accomplished in many ways, including but not limited to: physically touching (wiping) a sampling substrate across a surface and then inserting the sampling substrate in a detector or a removable sample holder for analysis and/or collecting the particle on a sampling substrate without contacting the surface followed by directly inserting the sampling substrate into the detector or removable sample holder.

Figure 8:
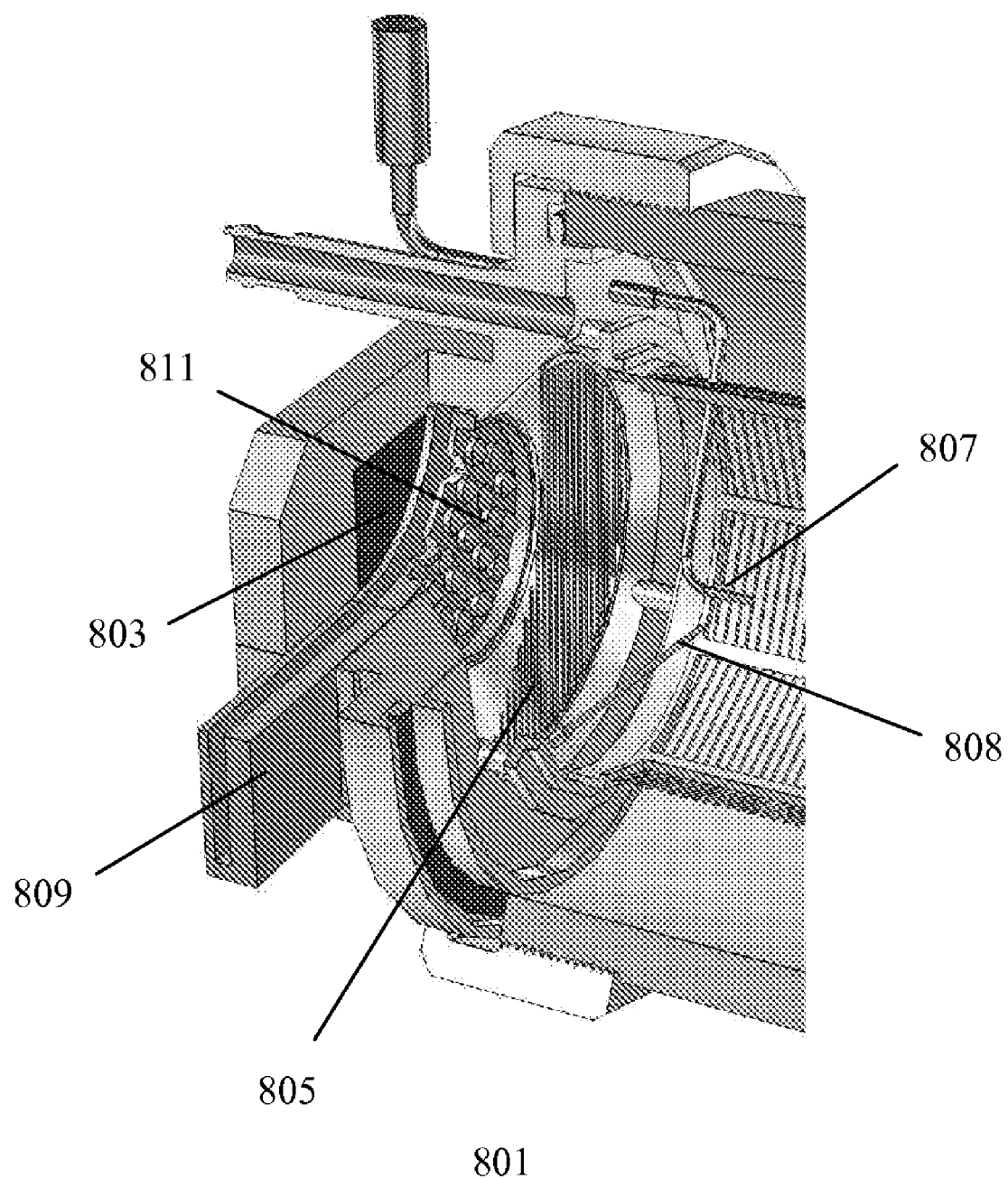
FIG. 8 schematically shows a multi-function sample introduction apparatus.

In a variety of embodiments, FIG. 8 shows the multifunction sample introduction apparatus 801. Utilizing the current sampling technique, i.e. swipe (swabbing) and particle desorption operation, the sampling substrate can be inserted into a sample loading port between the shaped heating plate 803 (thermal desorber) and sample inlet screen 805, in the location of the illustrated removable sample holder 809. As the samples are heated up with the temperature program, they are vaporized and transferred into the ionization chamber of the instrument by way of an opening and/or interface that has a gas outlet. The vaporized sample is ionized by an ionization source 807, such as a corona discharge source, but not limited to this source. The ionization chamber has an opening that accepts a sample in neutral and/or ionic form. For liquid sample introduction, a liquid inlet 808 is also included in the apparatus which can electrospray the liquid sample by applying a voltage. The removable sample holder 809 that that is illustrated in FIG. 8, containing a plurality of electrospray nozzles 811 can also be inserted into the multifunction sample introduction apparatus 801. With the electrospray capability, unknown liquids can be placed on the sample substrate and electrosprayed into the spectrometer. The multi-function sample introduction apparatus 801 can be interfaced to a variety of instruments, such as a MS, a ion mobility based spectrometer, in particular a high thermal conductivity IMS, but not necessarily limited to these.

One embodiment of the invention relates to transferring the sampling substrate to a removable sample holder prior to analysis. The removable sample holder comprises: a substantially sealed inner chamber, at least one opening for releasing a sample to a spectrometer, and at least one opening to receive the sample. In addition, the removable sample holder may include a single or plurality of electrospray nozzles, an electrical contact, and/or a porous material, such as foam, sponge, zeolite, membrane, metallic foam, but not limited to these that a applied solvent can flow. The removable sample holder body can be made from a number of materials that are inert from outgasing and/or experience chemical changes in their composition while being exposed to any solvents or mixtures of solvents, in addition the removable sample holder can be made from a material that can withstand rapid heating from low to high temperatures. The removable sample holder body may include an identification marking, such as a bar code or rf tag, but not necessarily limited to these. The solvents or mixtures of solvents that may be applied to the porous material may include; water, acetonitrile, alcohols, in particular, methanol and ethanol, hydrocarbons, in particular, hexane and pentane, halogenated, in particular methylene choride and chloroform, ketones, in particular acetone, but not limited to these; any suitable solvent or mixture of solvents that can dissolve the sample for use in a electrospray process.

In some embodiments, where the removable sample holder will be used for multiple sample introductions, the removable sample holder can be delivered in a sealed bag. Removal of the bag or solvent sealing strip makes the removable sample holder ready for use. The removable sample holder can be re-used for multiple sampling substrates (swabs). One sample introduction method would comprise: loading a known amount of sample into the removable sample holder, then inserting a removable sample holder into a sample loading port, and vaporizing some sample under a controlled temperature and/or temperature gradient into the ionization chamber. Another substrate sampling introduction method comprises: swabbing a sample with a wet or dry swab, loading the sample into a removable sample holder, dissolving the un-dissolved sample, and then electrospraying the dissolved sample into a analytical instrument.

Figure 9A:
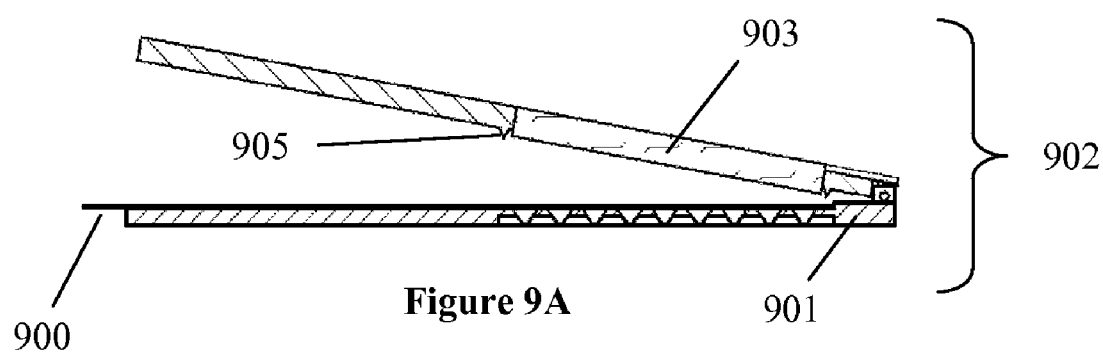
FIG. 9A-C are drawings that show the removable sample holder (9A shows the sample holder open with a sample swab inside, 9B shows the closed sample holder, and 9C shows the closed sample holder inside the multi-function sample introduction apparatus.
Figure 9B:
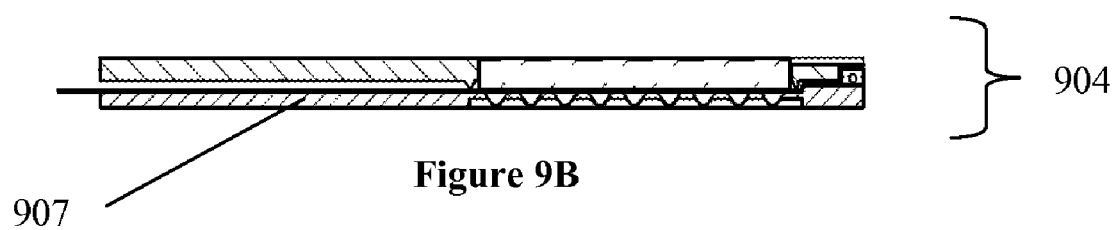
Figure 9C:
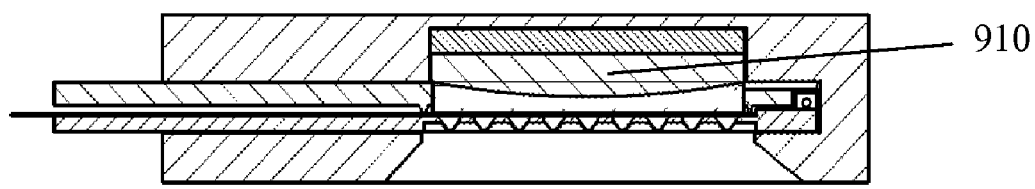

In a non limiting example of the removable sample holder being used for electrospray ionization, the sample substrate 900 is placed in an open removable sample holder 902 within which a porous material 903 is soaked with solvent or solvent mixture for electrospraying (FIG. 9A); when the removable sample holder is closed 904, the knife edge ring 905 will push down into the lower body 907 and form a seal around the electrospray nozzles thus forming a sealed inner chamber (FIG. 9B); as the sample holder is inserted between the shaped heating plate (at room temperature) and the sample inlet screen, the electrospray nozzles will be set at a higher voltage against the sample inlet screen. Meanwhile the shaped heating plate 910 will push into the porous material and create a higher pressure to start the electrospray (FIG. 9C). The removable sample holder may include an electrical contact 901 incorporated into the body and may also include at least one deformable surface that allows for increasing the pressure in the sealed inner chamber.

In one embodiment, the inner surface of the electrospray nozzle will be treated to be hydrophilic to the selected solvent and hydrophobic for the area surrounding the nozzle. When the holder is closed, the solvent will soak through the sample substrate and the dissolved samples will be accumulated in the electrospray nozzle with a local high concentration. Pulsed electrospray operation and positive and negative spray operation will be used to analyze both positive and negative ions.

A variety of materials, according to certain aspects of the invention, can be used to form any of the above-described components of the systems and devices of the invention. In some cases, the various materials selected lend themselves to various methods. For example, various components of the invention can be formed from solid materials that are inert. These inert materials should not outgas at elevated temperatures and/or experience chemical changes in their composition while being exposed to solvents, solvent mixtures, and/or heat. In one embodiment, the sampling substrate is made of a porous material such as cellulose, fabric, glass fiber and/or a fine wire mesh, multilayer diffusion bonded metal screens but not limited to only these materials. The screens can be made of, but not limited to, stainless steel, bronze, Monel, and other metal alloys. The opening of the screen may be in the range from sub-microns to hundreds of microns. The sampling substrate can be any size or shape that would be suitable for use in the described apparatus.

In another embodiment, the above-described porous material used for the sampling substrate can be chemically treated to assist in particle sampling, in particular for vapor sampling, the sample substrate may also be coated with a layer of affinitive material, such as modified PDMS used for SPME. Possible coating material may also include a functionalized surface, such as sol-gel. In addition to and including sampling vapors, the sampling substrate material may have chemical functionality covalently linked through the matrix of the material. These functional groups will assist in collecting the particles on the sampling substrate. For example, certain explosive materials are inherently sticky, such as C-4 (a RDX based explosive), and Deltasheet (PETN based explosive). Due to their makeup, these explosive molecules are generally greasy substances and are hydrophobic. Particles which are not explosive molecules can also be hard to remove from the surface and the methods disclosed below can be used not only for explosive molecules, but for particles in general. A non-limiting example of such functional groups are hydrophobic groups, such as an alkane, alkene, benzene derivative, haloalkane, but not limited to theses, that are chemically linked through a covalent bond to a cellulose matrix.

Figure 10:
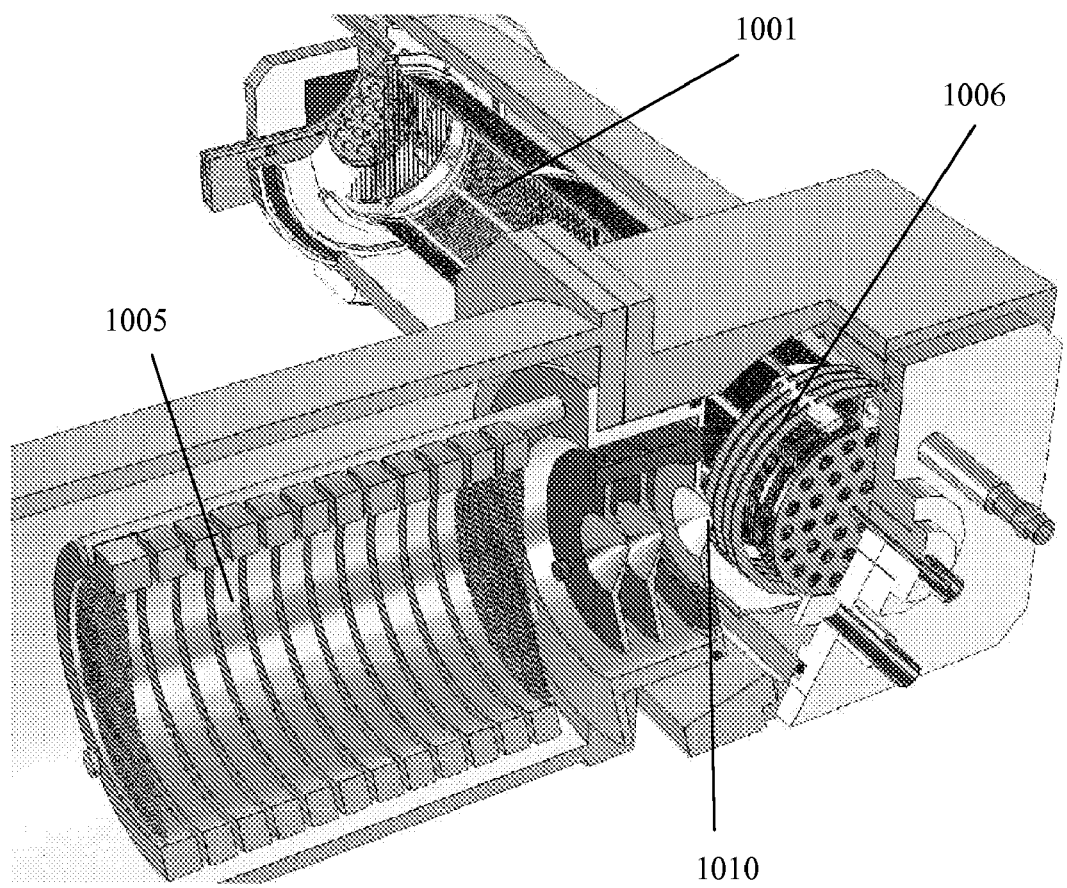
FIG. 10 schematically shows details of the interface between a orthogonal TOFMS and an IMS.

In alternative embodiments of the invention, the HTTD is used as sample introduction/pre-separation method for MS. Even though the HTTD has high resolution and is suitable for rapid screening of trace chemicals, the combination of HTTD and MS can provide addition technical merits. MS systems have greater resolution and the potential to reduce false alarm/identification rates for trace chemical detection applications. As most mass spectrometric instruments are configured for laboratory use, advanced sampling methods are required field trace detection applications. The HTTD can be interfaced to a MS as an integrated IMS-MS system. Compared to other types of MS, TOFMS may the advantage of higher resolution and rapid data acquisition. However, it also requires higher vacuum for operation, and it has been a major challenge to interface an atmospheric pressure IMS to a TOFMS because of the greater pressure difference. FIG. 10 shows the concept of interfacing the HTTD to the orthogonal interface 1005 of a TOFMS. In a variety of embodiments, the figure shows the HTTD 1001 is interfaced to a TOFMS (not shown) The mobility separated ions are extracted into the MS under vacuum through an interface assembly 1010 that may consist of, but not limited to, a pin-hole opening, single / multiple tube structure, or a slit opening in combination with skimmers and/or other ion optics commonly used for state of art MS. The ion extraction zone 1006 at the end of the HTTD and the interface assembly 1010 to MS are described in details in later sections. The integrated HTTD-MS detection system has improved selectivity and a versatile sample introduction apparatus as described in previously.

Figure 11:
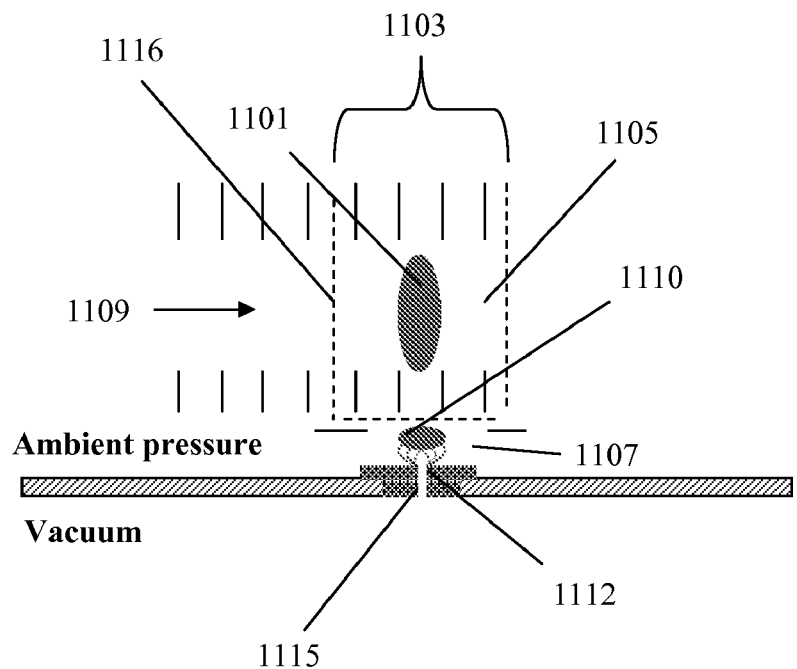
FIG. 11 schematically shows the mechanism of extracting ions in a transverse direction from the extraction zone into a vacuum inlet.

To resolve the ion transportation issues at IMS-MS interfaces, several ion extraction methods in front of MS interface are described in this invention. In a variety of embodiments, a novel multiple field zone ion extraction mechanism is described to extract ions in front of the vacuum inlet into the MS under vacuum conditions. FIG. 11 shows a non-limiting example of extracting mobility separated ions into the MS. When a group of mobility separated ions 1101 travels into the ion extraction zone 1103 through a grid 1116 that serve as a separator of the ion extraction zone and ion drift region, ions are kicked out from high field zone 1105 to a low field zone 1107 in front of the MS interface. In this low field zone, the "ion plug" is compressed in the direction that is perpendicular to its drift direction 1109 into a narrow band 1110. On the other hand, a high field zone 1112 is created by adding substantial voltage difference on each side of vacuum inlet tube 1115. The configuration of this inlet tube can be similar to a time of flight type IMS but with a small internal diameter. In particularly, the inlet tube can be made of a resistive glass tube. At the boundary area between high field zone 1112 and the low field zone 1107, an ion focusing effect can be achieved to extract ions from a larger area into the MS. As the ions are kicked out into this area, they can be transported into the MS with higher ion population. In a practical application, the high voltage ion kick out pulse is on for several microseconds. The ion extraction can be performed on the entire ion mobility spectrum or can selectively extract ions with mobilities of interest into the MS. As chemicals have already been ionized and separated in the HTTD, only chemicals that have the same ion mobility will be introduced into the MS during each kick out.

As discussed above, the method of mass analyzing mobility separated ions may involve generating ions in front of a IMS, separating ions in the IMS and transporting ions in the front of a vacuum inlet, collecting a section of mobility separated ions into the vacuum inlet in the direction that is perpendicular ion drift direction; and measuring mass to charge ratio in a MS. The method may also involve transporting ions into an ion extraction zone; and then compressing ions by applying a pulse of high electric field in the ion extraction zone, the ions are pushed into a low field zone in front of vacuum inlet. The ions are further transported and/or focused into the vacuum with assistance of a local high field inside the inlet and a gas flow. Alternatively, a method of introducing ions into a vacuum may involve transporting ions from a high pressure condition in to an ion extraction zone, and then compressing ions by applying a pulse of high electric field in ion extraction zone and push them into a low field zone in front of vacuum inlet; and further extracting ions into the vacuum inlet with another high electric field.

Figure 12:
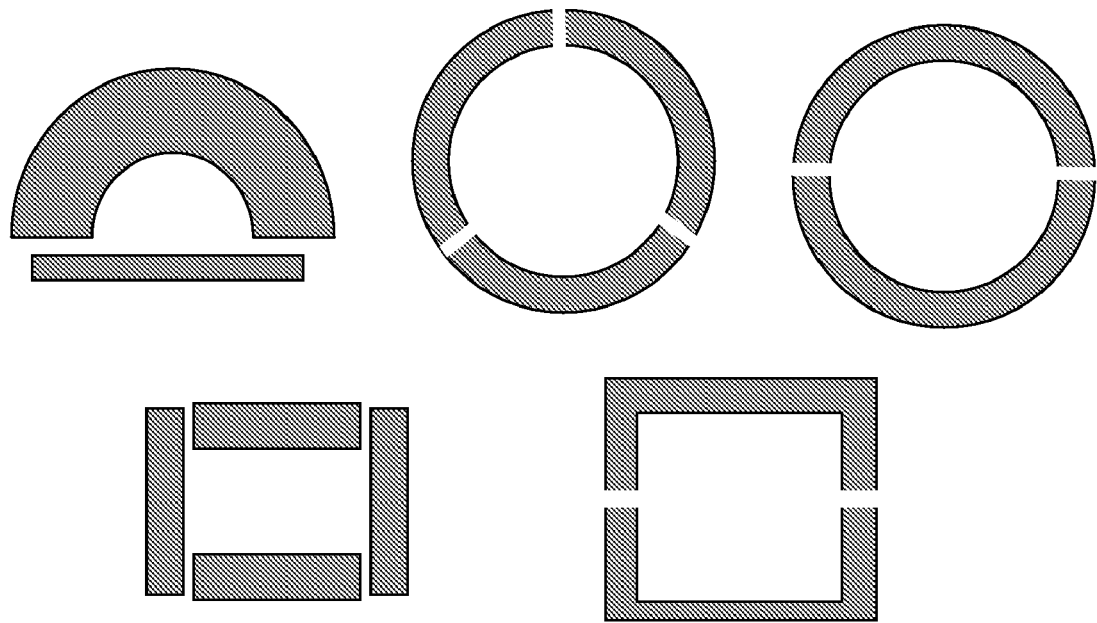
FIG. 12 schematically shows examples of drift ring or guard ring configurations for the extraction zone.

FIG. 12 shows examples of possible embodiments of drift ring or ion guide configuration for ion extraction zone. As shown in FIG. 12, many possible configurations can be used and the invention is not limited to a round ring shape structure. The electrodes are arranged to provide optimal electric field for the ion extraction and the maximum efficient for ion extraction.

Figure 13:
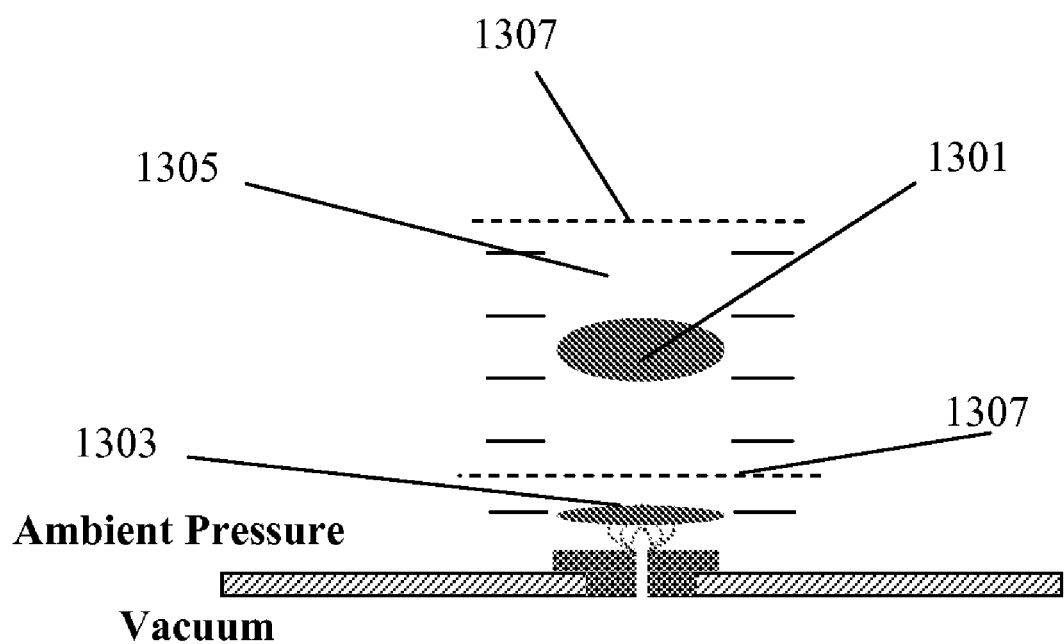
FIG. 13 schematically shows the mechanism of extracting ions in axial direction from the extraction zone into a vacuum inlet.

In FIG. 13, the mobility separated ions 1301 are compressed/condensed 1303 by the kick out voltage temporarily applied in the first high field zone 1305 that is defined by the field separator grid 1307 and an optional grid can as be placed between the high field (extraction) zone the vacuum inlet. The ion compression is in the direction that is in line with their drift direction. Compared to the method described in FIG. 11, the total amount of available ions can be less. The transverse field ion extraction can theoretically improve system sensitivity. An alternative embodiment of using transverse field ion extraction at the IMS-MS interface may not involve ion compression described in FIG. 11. Simply extract mobility separated ions into a MS in the direction that is perpendicular to their drift direction can provide better IMS-MS system sensitivity compared to inline IMS-MS interface that has be demonstrated in prior arts.

Figure 14:
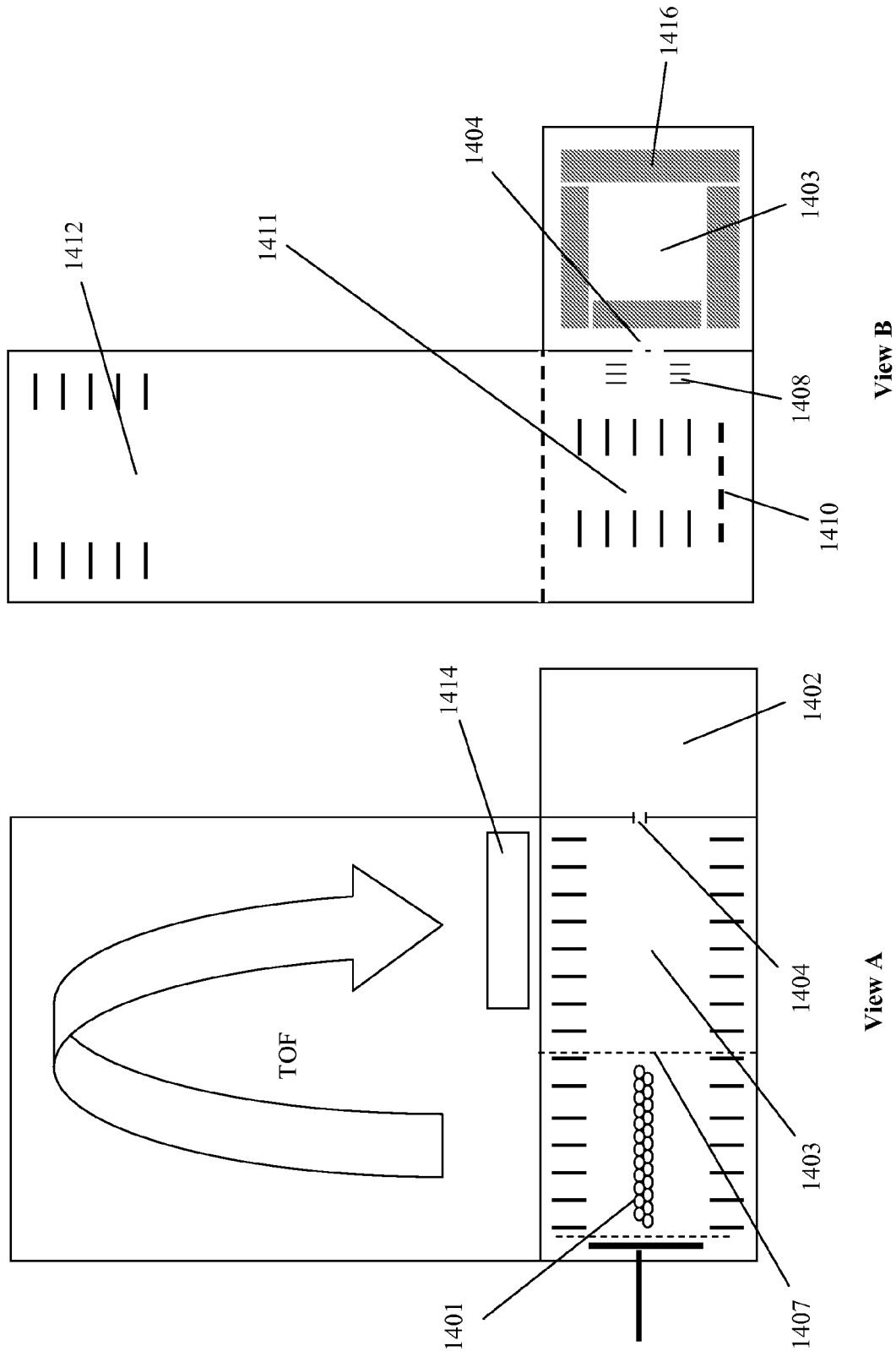
FIG. 14 schematically shows an example of IMS-MS interface; particularly an IMS is interfaced to an orthogonal TOFMS where ions are extracted from IMS in the transverse direction of their drift axis. Multi-dimensional IMS can be operated under different pressure conditions before mass analysis.

FIG. 14 shows the concept of one of the embodiments for interfacing an IMS to a TOFMS. An ion source 1402 is used for generating ions under ambient pressure conditions; An IMS 1403 having an inlet 1404 at first end accepting ion from the ionization source; As the ions are brought into the IMS, they are subsequently separated based on ion mobility along the drift axis; the ions enter ion extraction zone through a field separating grid 1407; the ion extraction zone locating in front of the vacuum inlet 1401 is designed to assist extracting ions from the IMS into the vacuum inlet in the direction that is substantially perpendicular to the ion drift axis; ions are kicked out from the ion extraction zone into a the vacuum inlet; the drift rings (or ion guide or guard rings) are segmented elements 1416 (View B) as described also in FIG. 12, where an extraction electric field can be created by applying a designed voltage on each element. During the ion kick out process, the normal ion drift electric field is temporarily converted to a strong electric field that is perpendicular to the drift axis, thus ions in the extraction zone are forced to move in the direction that is perpendicular to the original drift axis. The temporary ion extraction field is relatively short in time compared to ion drift time, thus ions outside the ion extraction zone can maintain their drift motion while ions in the extraction zone are forced toward the vacuum inlet. The ion extraction field is arranged to avoid mixing mobility separated ions during the extraction. As shown in the figure, the interface 1401 does not necessarily need to be a round orifice, pin-hole, or tubing; it could also be an array of pin-holes or an slit, or any other shape that allow multiple mobility separated ions entering the MS at same time. The figure shows an IMS-TOFMS interface; however, the interface could be used with other types of MS as well, such as, a microarray ion trap mass spectrometer, linear ion trap mass spectrometer, etc. Depending on the shape of the vacuum inlet, a section of mobility separated ion pockets are sampled into the vacuum inlet in the direction that is perpendicular to the ion drift direction. In a variety of embodiments, FIG. 14 shows a non-limiting example of using orthogonal TOFMS to measure mass to charge ratio of mobility separated ions. As ions are leaving IMS and enter the orthogonal interface 1408 (view B), they are directed into the ion accelerator 1411 by surrounding electric field and ion propeller 1410, if necessary; the ions fly through accelerator, field free region, reflectron 1412, and then to ion detector 1414. Note that instruments, such as MS and IMS, illustrated in this specification does represent accurate/complete configurations, they are used as non-limiting examples to show the concept of this invention; state of the art instruments, e.g. TOFMS, should be used in practice.

In addition, a multidimensional IMS can provide multiple step mobility separation prior to mass separation. As a multiple drift tube is used, each dimension of IMS drift tube may be operated under different pressure conditions. In FIG. 14, if the ionization source 1402 is replaced with a drift tube and the drift tube is operated under higher pressure conditions, the drift tube 1403 shown in this figure can be operated under a different pressure. With the first dimension drift tube at ambient pressure and second drift tube at medium pressure, e.g. from mTorr to 100s Torr, MS interfaced to second dimension drift tube may have a bigger opening, because of the reduced pressure difference between the second dimension drift tube and vacuum chamber for MS, the ion transfer efficiency can be improved. In summary, the apparatus of mass analyzing mobility separated ions using a first IMS having an inlet accepting ions from an ion source and subsequently mobility separating ions under a first pressure condition along a first axis; with multidimensional IMS, at least one higher order IMS can receive ions from the first IMS and subsequently mobility separating them under other pressure conditions along axes that is orthogonal to the first IMS; and an MS having an interface receiving a section of mobility separated ions for mass analysis. Note that the MS does not necessary to be a TOFMS, the method shall apply to operating a multidimensional IMS with any analytical instruments.

Without a multidimensional IMS, the drift tube can also be operated under medium pressure; a similar effect on ion transportation efficiency is expected. As shown in the figure, mobility separated ions are introduced into a TOFMS in the direction that is perpendicular to the flight path of ions in the TOFMS. The initial energy difference effect to the TOFMS resolution is eliminated by accelerating ions into the direction that is orthogonal to the sample inlet. Ions with a different mobility may be introduced into the vacuum chamber simultaneously and detected at different regions on the TOFMS detector without loss of ion mobility information. The spatial resolution on the detector can also be used for the ion identification based on both mass to charge ratio and ion mobility, thus improving the systems detection specificity.

Figure 15:
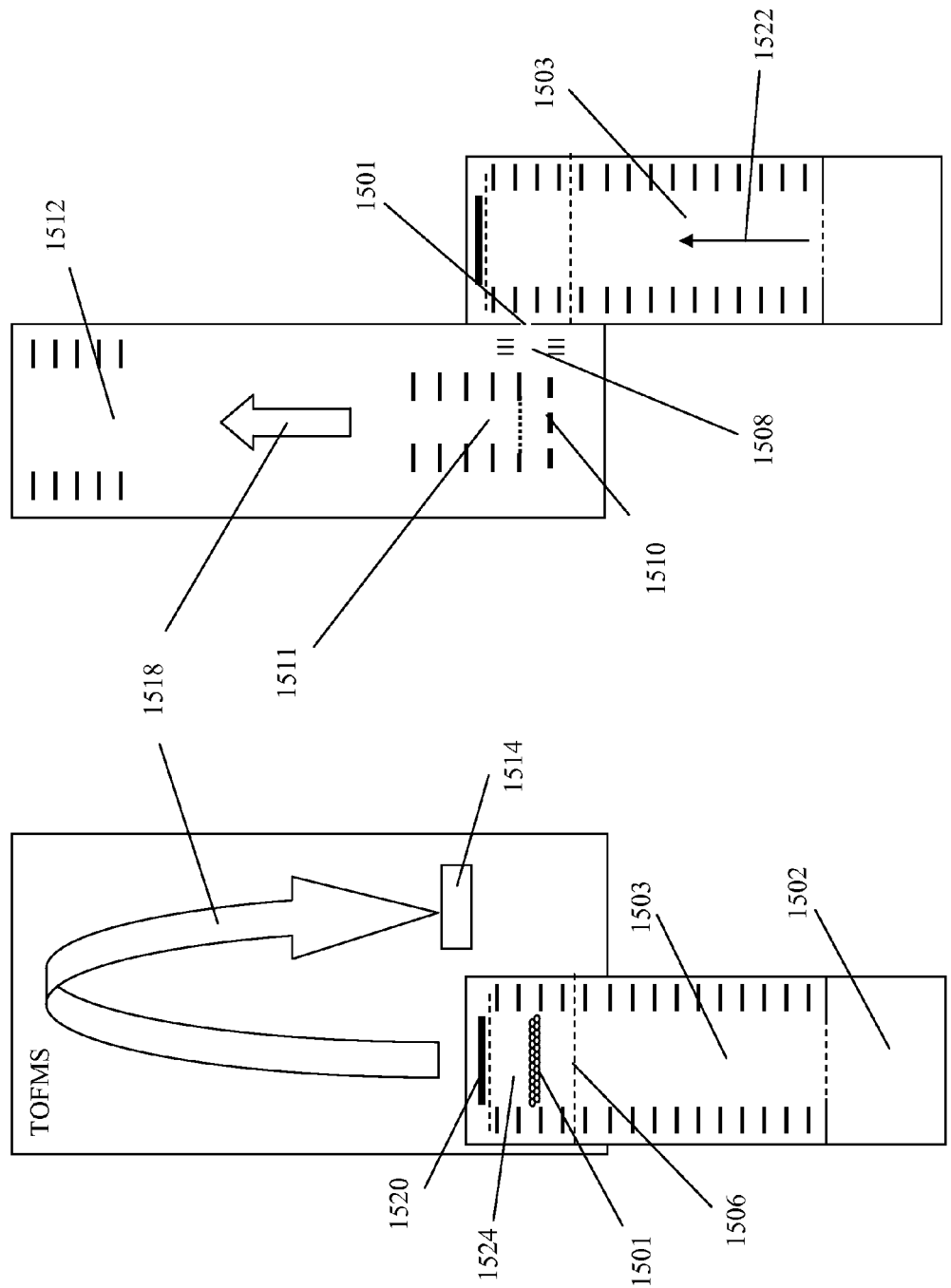
FIG. 15 schematically shows a preferred embodiment of the IMS and orthogonal TOFMS interface where the drift axis is parallel to the flight axis in the TOFMS. A vacuum inlet with an array of pinholes is shown to demonstrate effective sampling of a portion of mobility separated ions in transverse direction.

In a variety of embodiments, FIG. 15 shows a non-limiting example of IMS-TOFMS configuration. In FIG. 15A, the vacuum inlet 1501 is shown as an array of pin-holes, however, the inlet could be a round orifice, pin-hole, or tubing, or a slit, or any other shape that could serve as the barrier of vacuum and high pressure interface. In the shown example, the vacuum inlet has a shape that is similar to the projected profile of mobility separated ion pockets. When ions are generated in the ion source 1502 and introduced to the IMS via a inlet 1502 on one end, mobility separated ions pass through the field separator 1506, being extracted from the extraction zone 1524 in the direction that is perpendicular to their drift direction 1522; therefore a larger section of the mobility separated ion pocket could be brought into the orthogonal interface 1508 of the TOFMS. Alternatively, mobility separated ions can be detected by a detector 1520 under high pressure conditions. Subsequently the ions are kicked into the ion accelerator 1511 by repeller plate 1510 into the flight axis of the TOFMS and detected at the TOFMS ion detector 1514; a reflectron 1512 could be used for improved TOFMS performance. In the specific example shown in FIG. 15 A and B, the direction of the flight axis 1518 is parallel to the ion drift direction 1522. With a vacuum inlet having a shape that matches the side view cross section of ion pocket, orthogonally extracting ions into the MS provides a great benefit of ion transportation efficiency through the vacuum inlet. In general, when IMS ion outlet and TOFMS ion inlet (together shown as 1501 in FIG. 15B) matches, the TOFMS flight axis 1518 and IMS drift axis 1522 can be arranged in any angle or angles depending on the instrument design needs, especially when a symmetric vacuum inlet, e.g. round, square, is used. With the example shown in FIG. 15, having the flight axis 1518 and drift axis 1522 arranged substantially parallel (zero degrees) and/or anti-parallel (180 degrees) is preferred.

What is claimed is:

1. A multi-function sample introduction apparatus comprising: a sample loading port allows introducing a sample into an analytical instrument using a thermal desorber and/or an electrospray apparatus which both function in the same sample introduction apparatus; and an opening and/or interface to an ionization chamber of the analytical instrument.

2. The multi-function sample introduction apparatus of claim 1; wherein the sample loading port will accept a removable sample holder for direct insertion.

3. The multi-function sample introduction apparatus of claim 1; wherein the thermal desorber has a temperature programmable component.

4. The multi-function sample introduction apparatus of claim 3; wherein the thermal desorber has a shaped heating plate that is tailored to press onto the removable sample holder.

5. The multi-function sample introduction apparatus of claim 1; wherein the opening and/or interface have a gas outlet to bring a sample to the ionization chamber.

6. The multi-function sample introduction apparatus of claim 1; wherein the ionization chamber has a opening that accepts a sample in neutral and/or ionic form.

7. The multi-function sample introduction apparatus of claim 1; wherein the ionization chamber has an electric field that guides a sample toward an ion analyzer.

8. The multi-function sample introduction apparatus of claim 1; further comprises an ionization source that ionizes neutral molecules that enter the ionization chamber.

9. A removable sample holder for sample analysis comprising: a thermal desorption and/or electrospray ionization function in the same sample holder;
a means to receive the sample in liquid and/or solid form; a substantially sealed inner chamber; and at least one opening facing an analytical instrument having a function of releasing sample as vapor or charge liquid via an electrospray mechanism.

10. The removable sample holder of claim 9; wherein the sample is on a substrate.

11. The removable sample holder of claim 9; further comprises solvents and/or mixtures of solvents contained in a porous material.

12. The removable sample holder of claim 9; further comprises at least one deformable surface that allows for increasing a pressure in the sealed inner chamber.

13. The removable sample holder of claim 9; wherein the opening for releasing the sample is an electrospray nozzle.

14. The removable sample holder of claim 9 further comprises a hydrophilic coating on the inner surface and a hydrophobic coating surrounding the nozzle inlet area.

15. A sample introduction method comprising: loading a sample into a removable sample holder; inserting the removable sample holder into a sample loading port; and vaporizing some sample under a controlled temperature and/or temperature gradient into the ionization chamber using a thermal desorber or electrospraying the sample into an analytical instrument using the same sample holder.

16. The multi-function sample introduction apparatus of claim 1; further comprises at least one liquid inlet that introduces liquid samples into the ionization chamber.

17. The multi-function sample introduction apparatus of claim 16; wherein the liquid inlet has a means to apply a voltage for electrospraying a liquid sample.

18. A multi-function sample introduction method comprising:
introducing a sample into an analytical instrument using a sample port that allows thermal desorption and/or electrospray which both function in the same sample introduction apparatus; and transporting the sample to an ionization chamber of the analytical instrument through an opening and/or interface.

19. The sample introduction method of claim 15 wherein the sample is obtained by swabbing the sample with a wet or dry swab.

20. The sample introduction method of claim 15 further comprises dissolving the un-dissolving sample in the removable sample holder.

21. The sample introduction method of claim 15 further comprises deforming at least one surface of the removable sample holder to start the electrospray process.

* * * * *